United States Patent
Hwang et al.

(10) Patent No.: US 8,762,074 B2
(45) Date of Patent: Jun. 24, 2014

(54) OPTIMIZING CULTURE MEDIUM FOR CD34<+> HEMATOPOIETIC CELL EXPANSION

(75) Inventors: Shiaw-Min Hwang, Taipei (TW); Chi-Hsien Liu, Taipei (TW); Chao-Ling Yao, Taipei (TW); I-Ming Chu, Taipei (TW); Tzu-Bou Hsieh, Taipei (TW)

(73) Assignee: Sino-Cell Technologies, Taipei (TW)

( * ) Notice: Subject to any disclaimer, the term of this patent is extended or adjusted under 35 U.S.C. 154(b) by 0 days.

(21) Appl. No.: 13/468,253

(22) Filed: May 10, 2012

(65) Prior Publication Data

US 2012/0220032 A1 Aug. 30, 2012

Related U.S. Application Data

(60) Continuation-in-part of application No. 12/123,423, filed on May 19, 2008, now abandoned, which is a division of application No. 10/909,370, filed on Aug. 3, 2004, now abandoned.

(51) Int. Cl.
| | |
|---|---|
| *G01N 33/48* | (2006.01) |
| *G01N 33/50* | (2006.01) |
| *G01N 31/00* | (2006.01) |
| *G06F 7/60* | (2006.01) |
| *G06F 17/10* | (2006.01) |
| *G06F 19/24* | (2011.01) |
| *G06F 19/12* | (2011.01) |
| *G06F 19/28* | (2011.01) |
| *G06F 17/15* | (2006.01) |
| *G06F 17/11* | (2006.01) |

(52) U.S. Cl.
CPC .............. *G06F 19/24* (2013.01); *G06F 19/12* (2013.01); *G06F 19/28* (2013.01); *G06F 17/15* (2013.01); *G06F 17/11* (2013.01)
USPC ................... 702/21; 702/19; 702/22; 702/27; 703/2

(58) Field of Classification Search
None
See application file for complete search history.

(56) References Cited

PUBLICATIONS

Yao et al. Factorial designs combined with the steepest ascent method to optimize serum-free media for ex vivo expansion of human hematopoietic progenitor cells. Enzyme and Microbial Technology, vol. 33, 2003, pp. 343-352.*
Yao et al. A systematic strategy to optimize ex vivo expansion medium for human hematopoietic stem cells derived from umbilical cord blood mononuclear cells. Experimental Hematology, vol. 32, 2004, pp. 720-727.*
George E. P. Box et al., Fractional Factorial Designs at Two Levels, Statistics for Experimenters: An Introduction to Design, Data Analysis, and Model Building, p. 374-415, 418-419, 1978.
Marija J. Norusis, Multiple Response Analysis, SPSS for Windows Base System User's Guide Release 6.0, 1993, pp. 234, 238, 242, and 244.
Douglas C. Montgomery, Introduction to Factorial Design, Design and Analysis of Experiments, 1996, p. 230-289.
Douglas C. Montgomery, The 2k Factorial Design, Design and Analysis of Experiment, 1996, p. 290-353.
Douglas C. Montgomery, Blocking and Confounding in the 2kFactorial Design, Design and Analysis of Experiments, 1996, p. 354-371.
Douglas C. Montgomery, Two-level Fractional Factorial Designs, Design and Analysis of Experiments, 1996, p. 372-435.
Douglas C. Montgomery, The Method of Steepest Ascent, Design and Analysis of Experiments, 1996, p. 578-585.

* cited by examiner

*Primary Examiner* — Russell S Negin
(74) *Attorney, Agent, or Firm* — WPAT, P.C.; Anthony King; Kay Yang

(57) ABSTRACT

The present invention provides a method of determining the optimal composition of a serum-free, eukaryotic cell culture medium supplement, using 2-level factorial design and the steepest ascent method. The invention further provides a method of making a serum-free eukaryotic cell culture medium supplement and the generated thereof. The invention further provides a method of making a serum-free, eukaryotic cell culture medium and the medium generated thereof. The invention further provides a kit containing the medium of the invention. The invention also provides a method of expanding CD34<+> hematopoietic cells and a composition comprising CD34<+> hematopoietic cells in a serum-free, eukaryotic cell culture medium of the invention.

9 Claims, 2 Drawing Sheets

OPTIMIZING CULTURE MEDIUM FOR CD34<+> HEMATOPOIETIC CELL EXPANSION

CROSS REFERENCE TO RELATED APPLICATIONS

This application is a continuation-in-part under 35 U.S.C. §120 of U.S. application Ser. No. 12/123,423 filed on May 19, 2008, which is a division of U.S. application Ser. No. 10/909,370, filed on Aug. 3, 2004.

FIELD OF THE INVENTION

The present invention is in the field of ex vivo culture of hematopoietic cells, more specifically in the culture of hematopoietic stem cells and progenitor cells.

DESCRIPTION OF PRIOR ART

The hematopoietic stem cell can develop into multiple lineages, with a continuum of differentiation stages within each lineage. The final products are diverse, ranging from the non-nucleated red blood cells and platelets, to the highly complex macrophages and T cells, which have multiple physiological functions.

CD34 is a surface glycoprotein of unknown function that is found on approximately 1% of collected mononuclear cells (MNCs). It is present on all of the most primitive cells, from the quiescent stem cells to the highly proliferative cells. As nearly all the proliferative potential of hematopoietic cell culture is represented by these CD34<+> cells, cultured initiated with CD34<+> cells have much greater expansion potential than MNCs. In the other hand, CD34<+> cell populations also lack accessory cells such as macrophages that may provide cytokines and other stimulatory factors in MNC cultures.

In the mid 1960's, in order to better understand the mechanisms of normal and aberrant hematopoiesis, investigators began trying to grow bone marrow cells ex vivo using both suspension and semi-solid tissue culture systems. The early studies of Bradley and Metcalf (Bradley, T. R. and Metcalf, D., *Biol. Med. Sci.* 44:287-300 (1966)), as well as those of Pluznik and Sachs (Pluznik, D. H. and Sachs, L., *Expl. Cell Res.* 43:553-563 (1966)), demonstrated that in addition to serum, cell growth required the presence of factor, secreted by other cells (i.e. feeder cells) and found in the conditioned media from cultures of these cells. It is now clear that the growth of hematopoietic tissue ex vivo requires the presence of several cytokines or hematopoietic growth factors.

Several distinct factors have been identified, cloned and are now routinely manufactured as recombinant molecules for both research and/or clinical use. These include erythropoietin, interleukin-3 (IL-3), granulocyte macrophage-colony stimulating factor (GM-CSF), granulocyte-colony stimulating factor (G-CSF), stem cell factor (SCF), and interleukin-11 (IL-11), to cite only a few.

There are, however, serious disadvantages to the use of animal serum in a clinical setting: 1) the possible presence of an animal-transmitted microorganism; 2) the possibility of immune reaction to traces of animal protein, which reaction could lead to anaphylactic shock and death; 3) even if the animal protein were completely removed prior to infusion of the cells, it is possible that the exposure of the human cells to animal protein during the culture period would change their nature in a detrimental way.

There are also disadvantages to the use of human serum or plasma in ex vivo culture: 1) the possible presence of microorganisms, especially in pooled human serum; 2) the unpredictability of results, especially when using serum or plasma from a single donor or the patient's autologous serum, and; 3) the lack of a consistent source of sufficient plasma from a single donor.

In view of the many problems associated with the use of serum in the growth of CD34<+> cells, laboratories performing work with CD34<+> cells have attempted to replace animal sera or conditioned media with serum-free culture media of varying degrees of chemical definition. These attempts have met with varying degrees of success, depending upon the identity of the cell type one is trying to expand.

For example, WO 9,639,487 discloses a serum-free medium for culturing human mesenchymal precursor cells. U.S. Pat. No. 5,405,772 discloses a serum-free or serum-depleted medium for culturing hematopoietic cells and bone marrow stromal cells. U.S. Pat. No. 4,972,762 discloses a serum-free medium, containing penicillamine and N-acetylcysteine, for growing hybridomas and lymphoid cells. US 2001/0033835 discloses a serum-free medium for expansion of CD34<+> hematopoietic cells and cells of myeloid lineage.

The conventional method of optimization involves varying one parameter at a time and keeping the others constant. This often does not bring about the effect of interaction of various parameters as compared to factorial design (Cochran, W. G., and Cox, G. M. Experimental designs, $2^{nd}$ ed. John Wiley and sons, New York, pp. 335-375, (1992)). When an experimenter is interested in the effects of two or more independent variables, it is more efficient to manipulate these variables in one experiment than to run a separate experiment for each variable. Moreover, only in experiments with more than one independent variable is it possible to test for interactions among variables.

It is clear that when more than one growth factor is used, the choice and optimum amount of each factor should be determined in combination with the other factors to be used and will vary depending on the purity and method of production of the factors. This is because some growth factors can modulate the activity of other growth factors, or while in other instances, growth factors may act synergistically. Still other growth factors may enhance proliferation or differentiation along one pathway, while suppressing another pathway of interest. The choice and optimum quantity of each growth factor to be used in previous disclosures, however, was determined empirically or by most laborious experiments.

A 2-level factorial design for optimizing microbial animal cell media has proven useful (Liu, C. H. and Liao, C. C. *Biotechnol Lett* 16:801-6 (1994), Liu, C. H., *Enzyme Microb Technol* 28:314-21 (2001), Chen, K. C., *Enzyme Microb Technol* 14:659-64 (1992), Chang Y N, *Enzyme Microb Technol* 30:889-94 (2002), Box, G. E. P., New York: Wiley, p. 374-418 (1978)). It is a powerful technique for testing multiple component variables because fewer experimental trials are required to implement it. However, this technique has not been applied to optimize the factors (cytokines, serum substitutes) in HSC expansion medium.

SUMMARY OF THE INVENTION

The invention provides a method of determining the optimum composition of a serum-free, eukaryotic cell culture medium supplement, comprising:
a. determining the cytokine to be used by 2-level factorial design;
b. determining the optimal quantity of cytokine to be used by steepest ascent method;

c. determining the serum substitute to be used by 2-level factorial design; and
d. determining the optimal quantity of cytokine to be used by steepest ascent method,
wherein the basal cell culture medium supplemented with the supplement is capable of supporting the expansion of CD34<+> hematopoietic cells and in serum-free culture.

The invention further provides a method of making a serum-free eukaryotic cell culture medium supplement, comprising admixing water with one or more ingredients of quantity determined by method of the present invention, wherein the supplement is capable of supporting the expansion of CD34<+> hematopoietic cells and in serum-free culture.

The invention also provides a serum-free, eukaryotic cell culture medium supplement made by method of the present invention, wherein the supplement is capable of supporting the expansion of CD34<+> hematopoietic cells and in serum-free culture.

The invention further provides a kit comprising a carrier means, the carrier means being compartmentalized to receive in close confinement therein one or more container means, wherein a first container means contains the medium supplement of the present invention, and wherein optionally a second container means contains a basal culture medium.

The invention also provides a method of making a serum-free, eukaryotic cell culture medium comprising admixing a basal cell culture medium with the medium supplement of the invention, wherein the medium is capable of supporting the expansion of CD34<+> hematopoietic cells.

The invention further provides a serum-free, eukaryotic cell culture medium obtained by the method of the invention, wherein the medium is capable of supporting the expansion of CD34<+> hematopoietic cells and in serum-free culture.

The invention also provides a method of expanding CD34<+> hematopoietic cells, said method comprising
(a) contacting said cells with the medium of the invention; and
(b) culturing said cells under conditions suitable to facilitate the expansion of said cells.

The invention further provides a composition comprising CD34<+> hematopoietic cells in a serum-free, eukaryotic cell culture medium of the invention.

DETAILED DESCRIPTION OF THE INVENTION

Term Definition

Figure 1:
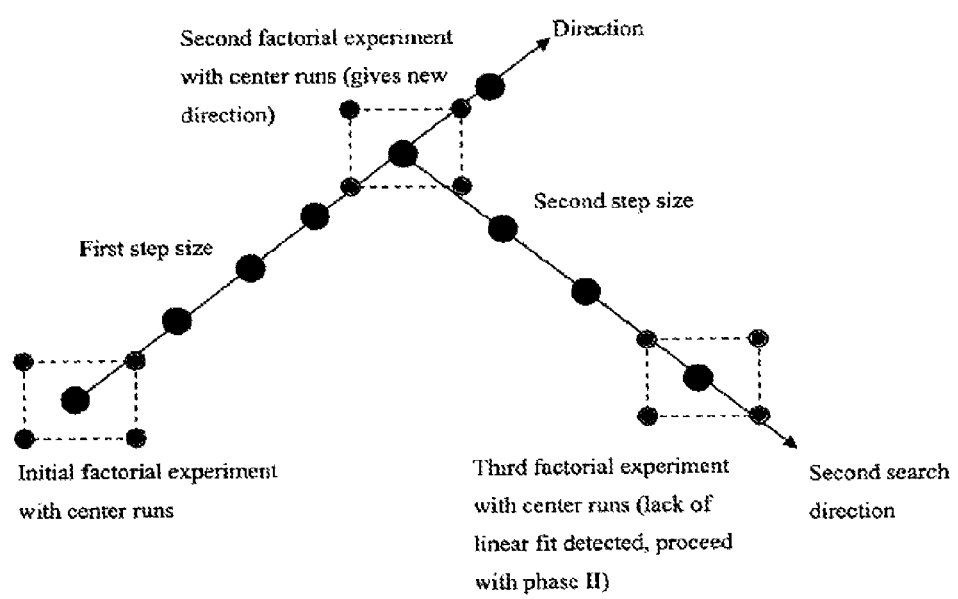
FIG. 1 illustrates a sequence of line searches when seeking a region where curvature exists in a problem with 2 factors (i.e., k=2).

Unless defined otherwise, all technical and scientific terms used herein have the same meaning as commonly understood by those of ordinary skill in the art to which this invention belongs. Although any methods and materials similar or equivalent to those described herein can be used in the practice or testing of the present invention, the preferred methods and materials are described. For purposes of the present invention, the following terms are defined below.

The terms "isolated", "purified" or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography. A protein that is the predominant protein present in a preparation is substantially purified. Generally, an isolated protein molecule will comprise more than 80% of all macromolecular species present in the preparation. Preferably, the protein is purified to represent greater than 90% of all macromolecular species present. More preferably the protein is purified to greater than 95%, and most preferably the protein is purified to essential homogeneity, wherein other macromolecular species are not detected by conventional techniques.

The terms "polypeptide" and "protein" refers to a polymer of amino acid residues. The terms apply to amino acid polymers in which one or more amino acid residue is an artificial chemical analogue of a corresponding naturally occurring amino acid, as well as to naturally occurring amino acid polymers. The term "recombinant protein" refers to a protein that is produced by expression of a nucleotide sequence encoding the amino acid sequence of the protein from a recombinant DNA molecule.

The term "serum" as used herein means the liquid portion of the blood that remains after blood cells and fibrinogen/fibrin are removed. The term "serum-free culture medium" means a culture medium containing no serum of animals and especially those originating from mammals, birds, fish or crustaceans. As regards the culture medium, it may have a chemically defined composition or a composition that is not chemically defined if it contains, for example, extracts of microorganisms, of yeasts or of fungi or even of plants that are not chemically well characterized.

The invention provides a method of determining the optimum composition of a serum-free, eukaryotic cell culture medium supplement, comprising:
e. determining the cytokine to be used by 2-level factorial design;
f. determining the optimal quantity of cytokine to be used by steepest ascent method;
g. determining the serum substitute to be used by 2-level factorial design; and
h. determining the optimal quantity of cytokine to be used by steepest ascent method,
wherein the basal cell culture medium supplemented with the supplement is capable of supporting the expansion of CD34<+> hematopoietic cells and in serum-free culture.

The 2-level factorial design or steepest ascent method in present invention can be performed by software package, especially a statistic software package, such as SPSS.

The invention further provides a method of making a serum-free eukaryotic cell culture medium supplement, comprising admixing water with one or more ingredients of quantity determined by method of the present invention, wherein the basal cell culture medium supplemented with the supplement is capable of supporting the expansion of CD34<+> hematopoietic cells and in serum-free culture.

By way of example, a brief description of the 2-level (full or fractional) factorial design and steepest ascent method follows:

2-Level ($2^k$) Factorial Design

The choice of cytokine and serum substitute to be used is determined by 2-level factorial design. Because each complete replicate of the design has $2^k$ runs, the arrangement is also called a $2^k$ factorial design. As the name shows, variables in 2-level factor design have only two levels, usually denoted "high" and "low" or "presence" and "absence".

Taking the two-level, full factorial design for three factors, namely the $2^3$ design, as an example. In tabular form, this design is given by:

TABLE 1

| run | X1 | X2 | X3 |
|-----|----|----|----|
| 1 | −1 | −1 | −1 |
| 2 | 1 | −1 | −1 |
| 3 | −1 | 1 | −1 |
| 4 | 1 | 1 | −1 |
| 5 | −1 | −1 | 1 |
| 6 | 1 | −1 | 1 |
| 7 | −1 | 1 | 1 |
| 8 | 1 | 1 | 1 |

The left-most column of Table 1, numbers 1 through 8, specifies a (non-randomized) run order called the "Standard Order". For example, run 1 is made at the 'low' setting of all three factors.

We can readily generalize the $2^3$ standard order matrix to a 2-level full factorial with k factors. The first (X1) column starts with −1 and alternates in sign for all $2^k$ runs. The second (X2) column starts with −1 repeated twice, then alternates with 2 in a row of the opposite sign until all $2^k$ places are filled. The third (X3) column starts with −1 repeated 4 times, then 4 repeats of +1's and so on. In general, the i-th column ($X_i$) starts with $2^{i-1}$ repeats of −1 followed by $2^{i-1}$ repeats of +1.

For example, an engineering experiment called for running three factors; namely, Pressure (factor X1), Table speed (factor X2) and Down force (factor X3), each at a 'high' and 'low' setting, on a production tool to determine which had the greatest effect on product uniformity. Two replications were run at each setting. A (full factorial) $2^3$ design with 2 replications calls for 8*2=16 runs.

TABLE 2

Model or analysis matrix for a $2^3$ experiment

| | Model Matrix | | | | | | | Response Variables | |
|---|---|---|---|---|---|---|---|---|---|
| Run | X1 | X2 | X1*X2 | X3 | X1*X3 | X2*X3 | X1*X2*X3 | Rep 1 | Rep 2 |
| 1 | −1 | −1 | +1 | −1 | +1 | +1 | −1 | −3 | −1 |
| 2 | +1 | −1 | −1 | −1 | −1 | +1 | +1 | 0 | −1 |
| 3 | −1 | +1 | −1 | −1 | +1 | −1 | +1 | −1 | 0 |
| 4 | +1 | +1 | +1 | −1 | −1 | −1 | −1 | +2 | +3 |
| 5 | −1 | −1 | +1 | +1 | −1 | −1 | +1 | −1 | 0 |
| 6 | +1 | −1 | −1 | +1 | +1 | −1 | −1 | +2 | +1 |
| 7 | −1 | +1 | −1 | +1 | −1 | +1 | −1 | +1 | +1 |
| 8 | +1 | +1 | +1 | +1 | +1 | +1 | +1 | +6 | +5 |

Running the full complement of all possible factor combinations means that we can estimate all the main and interaction effects. There are three main effects, three two-factor interactions, and a three-factor interaction, all of which appear in the full model as follows:

$$Y=\beta_0+\beta_1 X_1+\beta_2 X_2+\beta_3 X_3+\beta_{12} X_1*X_2+\beta_{23}*X_2*X_3+\beta_{13}X_1*X_3+\beta_{123}X_1*X_2*X_3,$$

wherein Y is the response variables, X is the operating conditions of factors, and β is regression coefficients which is obtained using the above formula. A full factorial design allows us to estimate all eight "beta" coefficients $\{\beta_0 \sim \beta_{123}\}$.

2-Level Fractional Factorial Design

Even if the number of factors, k, in a design is small, the $2^k$ runs specified for a full factorial can quickly become very large. For example, $2^6$=64 runs is for a two-level, full factorial design with six factors. Therefore it is very often to use only a fraction of the runs specified by the full factorial design, which is called 2-level ($2^k$) fractional factorial design. 2-level fractional factorial design containing $2^{k-p}$ runs experiments is also called a ½ p fraction of the $2^k$ design or, a $2^{k-p}$ fractional factorial design. Which runs to make and which to leave out is the subject of interest here. In general, we pick a fraction such as ½, ¼, etc. of the runs called for by the full factorial.

Consider the two-level, full factorial design for three factors, namely the $2^3$ design. This implies eight runs (not counting replications or center points).

In tabular form, this design (also showing eight observations "$y_j$" (j=1, ..., 8) is given by

TABLE 3

A $2^3$ full factorial design table showing runs in standard order, plus observations ($Y_j$)

| | X1 | X2 | X3 | Y |
|---|----|----|----|----|
| 1 | −1 | −1 | −1 | Y1 = 33 |
| 2 | +1 | −1 | −1 | Y2 = 63 |
| 3 | −1 | +1 | −1 | Y3 = 41 |
| 4 | +1 | +1 | −1 | Y4 = 57 |
| 5 | −1 | −1 | +1 | Y5 = 57 |
| 6 | +1 | −1 | +1 | Y6 = 51 |
| 7 | −1 | +1 | +1 | Y7 = 59 |
| 8 | +1 | +1 | +1 | Y8 = 53 |

The right-most column of the table lists '$y_1$' through '$y_8$' to indicate the responses measured for the experimental runs when listed in standard order. For example, "$y_1$" is the response (i.e., output) observed when the three factors were all run at their "low" setting. The numbers entered in the "y" column will be used to illustrate calculations of effects.

From the entries in the table we are able to compute all "effects" such as main effects, first-order "interaction" effects, etc. For example, to compute the main effect estimate "$c_1$" of factor $X_1$, we compute the average response at all runs with $X_1$ at the "high" setting, namely $(¼)(y_2+y_4+y_6+y_8)$, minus the average response of all runs with $X_1$ set at "low", namely $(¼)(y_1+y_3+y_5+y_7)$. That is, $$c_1=(¼)(y_2+y_4+y_6+y_8)-(¼)(y_1+y_3+y_5+y_7)$$

or $$c_1=(¼)(63+57+51+53)-(¼)(33+41+57+59)=8.5$$

Suppose, however, that we only have enough resources to do four runs. Is it still possible to estimate the main effect for $X_1$? Or any other main effect? The answer is yes, and there are even different choices of the four runs that will accomplish this.

For example, suppose we select only the four runs 1, 4, 6 and 7, we can still compute $c_1$ as follows:

$$c_1=(½)(y_4+y_6)-(½)(y_1+y_7)$$

or $$c_1=(½)(57+51)-(½)(33+59)=8.$$

Similarly, we would compute $c_2$, the effect due to $X_2$, as $$c_2=(1/2)(y_4+y_7)-(1/2)(y_1+y_6)$$

or $$c_2=(1/2)(57+59)-(1/2)(33+51)=16.$$

Finally, the computation of $c_3$ for the effect due to $X_3$ would be $$c_3=(1/2)(y_6+y_7)-(1/2)(y_1+y_4)$$

or $$c_3=(1/2)(51+59)-(1/2)(33+57)=10.$$

We could also have used the other four runs and obtained similar, but slightly different, estimates for the main effects. In either case, we would have used half the number of runs that the full factorial requires. The half fraction we used is a new design written as $2^{3-1}$. Note that $2^{3-1}=2^3/2=2^2=4$, which is the number of runs in this half-fraction design.

If the interaction effects are considered negligible, the $2^{3-1}$ design replicated twice requires only 4×2=8 runs, and then we would have 15−8=7 spare runs. As long as we are confident that the interactions are negligibly small (compared to the main effects), then the above replicated $2^{3-1}$ fractional factorial design (with center points) is a very reasonable choice.

The method to screen and select the proper cytokine and serum substitute for the medium supplement of the present invention is selected from using 2-level full fractional factorial design or 2-level fractional factorial design.

After selecting the proper cytokine or serum substitute by 2-level full fractional factorial design or 2-level fractional factorial design, the optimal quantity of each factor is determined by steepest ascent method.

Steepest Ascent Method

The Steepest-Ascent method is one of the main methods for finding the optimum conditions (optimum region). This method is used to move toward the regions of the response located near the optimum.

If experimentation is initially performed in a new, poorly understood production process, chances are that the initial operating conditions $X_1, X_2, \ldots, X_k$ are located far from the region where the factors achieve a maximum or minimum for the response of interest, Y. A first-order model will serve as a good local approximation in a small region close to the initial operating conditions and far from where the process exhibits curvature. Therefore, it makes sense to fit a simple first-order (or linear polynomial) model of the form:

$$Y=\beta_0+\beta_1 X_1+\beta_2 X_2+\ldots+\beta_k X_k,$$

wherein Y is response variables, X is the operating conditions of factors, and β is a regression coefficients which is obtained using the above formula according to current experiment results. The coefficient, β, reflexes the effects of factors. A factor with positive β means the factor has a positive effect of response variables, and the higher β value means the factor has stronger effect of response variables, vice versa. After β are all obtained, the present invention selects the factors with a positive β to perform the following steepest ascent method experiments.

Experimental strategies for fitting this type of model were discussed earlier. Usually, a $2^{k-p}$ fractional factorial experiment is conducted with repeated runs at the current operating conditions (which serve as the origin of coordinates in orthogonally coded factors).

The idea of the steepest ascent method is to keep experimenting along the direction of steepest ascent until there is no further improvement in the response.

At that point, a new fractional factorial experiment with center runs is conducted to determine a new search direction.

This process is repeated until at some point significant curvature in Y is detected. This implies that the operating conditions $X_1, X_2, \ldots, X_k$ are close to where the maximum of Y occurs. When significant curvature, or lack of fit, is detected, the experimenter should proceed with "Phase II". The phase II means finding a best operating condition by further adding repeating runs to find the best significant curvature, or choosing the operating condition of the run which is most close to the significant curvature. FIG. 1 illustrates a sequence of line searches when seeking a region where curvature exists in a problem with 2 factors (i.e., k=2).

The starting operating conditions in steepest ascent method mostly are set as a half operating condition of the factors in the 2-level (fractional) factorial design. In some case, for example, the experiment was proved can be performed in extremely low or without factors, the starting operating conditions will set as zero. Along the path of steepest ascent, the present invention increases or decreases the operating conditions each run of each factors in a ratio of:

$$\beta_1 \cdot \Delta X_1 : \beta_2 \cdot \Delta X_2 : \ldots : \beta_k \cdot \Delta X_k,$$

wherein the β is obtained by the simple first-order (or linear polynomial) model in steepest ascent method, ΔX is a difference between the +1 and −1 groups operating condition of X factor in 2-level (fractional) factorial design. The increased or decreased level of operating conditions are not limited being modified in a small range to make the operating conditions more easily being calculated, prepared or treated.

After a few steepest ascent searches, a first-order model will eventually lead to no further improvement or it will exhibit lack of fit. This condition is usually where the optimal operating conditions exist (FIG. 1).

Besides, the formula of steepest ascent method can further be used for estimating the maximum of Y and its' corresponding operating conditions. On the other hand, the most effective operating conditions of the factors can be estimated using the formula of steepest ascent method.

The optimal quantity of cytokines or serum substitutes of the medium supplement of the present invention is determined and adopted by the steepest ascent method. After the optimal quantity is found, the present invention further mixes it with various basal mediums and finds the best combination with the most favorable response of cell growth as the serum free and cytokine-contained cell culture medium.

Cytokines

The cytokines into which is incorporated according to the invention may be selected from the group known in the art to be supportive of ex vivo HSCs expansion, comprising interleukins (IL) 1-15, erythropoietin (EPO), stem cell factor (SCF, also known as mast cell growth factor and c-kit ligand (KL)), FLt-3 ligand (FL), granulocyte-colony stimulating factor (G-CSF), granulocyte, macrophage-colony stimulating factor (GM-CSF), macrophage-colony stimulating factor (M-CSF), tumor growth factor beta (TGF beta), tumor necrosis factor alpha (TNF alpha), the interferons (IFN alpha, beta, or gamma), fibroblast growth factor (FGF), platelet-derived growth factor (PDGF), insulin-like growth factors (IGF-1 and IGF-2) and Thyroid-derived chondrocyte stimulating factor (TDCSF), ciliary neurotrophic factor (CNTF), macrophage inflammatory protein 1 alpha (MIP-1alpha), antibody to the receptor c-kit (Kurosawa, K. et al, *Blood* 1996 87. 2235-2243), and thrombopoietin (TPO).

The cytokines into which is incorporated according to the invention may also be selected from the group of "designer" cytokines created to be supportive of ex vivo HSCs expansion, comprising PIXY321 (Curtis, B. M., et al. *Proc. Natl. Acad. Sci. U.S.A.* 1991 88. 5809-5813), Epo-IL-3 (Lu, L., et al. *Exp. Hematol.* 1995 23. 1130-1134), IL-2-IL-6 (Zhao. C., et al. *Stem Cells* 1994. 12. 1130-1134), Hyper-IL-6 (Peters, M., *J Immunol.* 1998 161:3575-81.) synthetic IL-3 (Thomas.

J. W., et al. *Proc. Natl. Acad. Sci. U.S.A.* 1995 92. 2859-2863), soluble IL-6 receptor (sIL-6-r). The cytokines into which is incorporated according to the invention may also be a combination of the cytokines described above. The growth factors are commercially available, for example, from R&D Systems (Minneapolis, Minn.). Particularly preferred are combinations of growth factors, especially the combination of SCF, IL-1 alpha, IL-3 and IL-6.

Serum Substitutes

The serum substitutes into which is incorporated according to the invention may be selected from the group known in the art to be supportive of ex vivo HSCs expansion, comprising Albumax, bovine serum albumin (BSA), transferrin (TF), glutamine, hydrocortisone (HC), peptone, 2-mercaptoethanol (2-ME), insulin, polyvinylpyrrolidone (PVP), Knockout Serum Replacement (KNOCKOUT™ SR, Invitrogen), Serum Replacement 1 (Sigma-Aldrich), Serum Replacement 2 (Sigma-Aldrich), Fetal Clone I (Hyclone), and Fetal Clone II (Hyclone).

In general, the above-mentioned proteins are purified or partially purified before they are added to the culture medium. Usually, they will be produced by recombinant DNA methods, but they may also be purified by standard biochemical techniques from conditioned media. Non-naturally-occurring growth factors can also be produced by recombinant DNA methods. For example, PIXY 321 is a fusion protein that has both GM-CSF and IL-3 activity. It will be evident to those skilled in the art that other fusion proteins, combining multiple growth factor activities, can be readily constructed. For example, fusion proteins combining SCF activity with that of other growth factors such as IL-1, IL-3, IL-6, G-CSF, and/or GM-CSF.

Basal Culture Medium

The basal culture medium into which is incorporated according to the invention may be selected from the group comprising MEM, MEM-[alpha], DMEM, RPMI, ISCOVE, Ham F12, HAM F10, M199, L15, 6M, or NCTC109 medium, Fischer medium, Waymouth medium, VPSFM medium (defined medium supplied by the company Gibco Life Technologies and having the reference number 11002086), Williams medium or mixtures of these basal media. These basal media may be enriched according to the needs of the cells, with additional nutrient factors such as, for example, sugars such as glucose, amino acids such as glutamine, a cocktail of nonessential amino acids or of essential amino acids or of peptides, acids or acid salts such as sodium pyruvate, EDTA salts, citric acid derivatives or more generally derivatives of acids involved in the Krebs cycle, alcohols such as ethanol, amino alcohols such as ethanolamine, vitamins such as vitamin C and vitamin E, antioxidants such as glutathione or selenium, fatty acids with saturated or unsaturated chains such as linoleic acid, arachidonic acid, oleic acid, stearic acid or palmitic acid, lipids or lipopeptides, and also with phospholipids such as lecithins. The addition of a buffer solution based on HEPES or bicarbonates may prove to be necessary for certain fragile cell cultures or for cultures producing large amounts of $CO_2$, or optionally to buffer culture media that are highly supplemented with acids. In general, care will be taken to ensure that the pH of the culture medium remains between 6 and 8, usually between 7 and 8 and more specifically between 7.2 and 7.5. As far as is possible, care will be taken to ensure that the culture medium remains isotonic.

The preferred basal cell culture medium is selected from the group consisting of IMEM, RPMI-1640 and a-MEM.

CD34<+> Cells

CD34<+> hematopoietic stem cells may be obtained from an animal selected from the group consisting of human, monkey, ape, mouse, rat, hamster, rabbit, guinea pig, cow, swine, dog, horse, cat, goat, and sheep. CD34<+> cells may be derived from umbilical cord blood (UCB), bone marrow, peripheral blood and fetal liver. The identification and selection of CD34<+> cells using fluorescence assays are well known in the art and are exemplified in the example. Equivalent hematopoietic cells are cells from non-human species that are regarded by those of ordinary skill in the art as HSCs.

The invention further provides a method of making a serum-free eukaryotic cell culture medium supplement, comprising admixing water with one or more ingredients of quantity determined by method of the present invention, wherein the basal cell culture medium supplemented with the supplement is capable of supporting the expansion of CD34<+> hematopoietic cells and in serum-free culture.

The invention also provides a serum-free, eukaryotic cell culture medium supplement made by the method of the invention, wherein the basal cell culture medium supplemented with the supplement is capable of supporting the expansion of CD34<+> hematopoietic cells and in serum-free culture. The medium supplement may be in a concentrated medium formulation. The preferred formulation of the supplement is greater than 10× concentrated.

The present invention also provides a kit comprising a carrier means such as a box or carton being compartmentalized to receive in close confinement therein one or more container means such as vials, tubes, ampules, jars, and the like, wherein a first container means contains the supplement of the present invention. Optionally, a second container means contains a basal medium.

Preferably, the container containing the supplement of the present invention can be stored from about −135 to about 4° C., preferably from about −5 to about −80° C., most preferably from about −5 to about −20° C., and still more preferably at about −20° C. A container containing the medium of the invention is preferably stored at about 2 to about 8° C., and most preferably at about 4° C.

The present invention also provides a method of making a serum-free, eukaryotic cell culture medium comprising admixing a basal cell culture medium with the medium supplement of the invention, wherein the medium is capable of supporting the expansion of CD34<+> hematopoietic cells.

The present invention further provides the serum-free, eukaryotic cell culture medium generated thereof.

The present invention also provides a method of expanding CD34<+> hematopoietic cells, said method comprising
(a) contacting said cells with the medium of the invention; and
(b) culturing said cells under conditions suitable to facilitate the expansion of said cells.

The present invention further provides a composition comprising CD34<+> cells in a serum-free medium, wherein the serum-free medium, which is supplemented with the serum-free supplement of the invention, is capable of supporting the growth of the CD34<+> hematopoietic cells in serum-free culture. Aliquots of this composition can be frozen at about −80° C. and below.

Aliquots of this composition can be stored indefinitely at less than or equal to about −135° C. After an aliquot of the composition has been thawed and opened, using sterile cell culture technique, the CD34<+> hematopoietic cells can be cultivated in serum-free culture. Animals from which CD34<+> cells can be obtained include human, monkey, ape, mouse, rat, hamster, rabbit, guinea pig, cow, swine, dog, horse, cat, goat, and sheep.

It is also routine to freeze hematopoietic cells for use at a later date.

The present invention further provides a method of expanding CD34<+> hematopoietic cells, said method comprising
(a) contacting said cells with the medium of the present invention; and
(b) culturing said cells under conditions suitable to facilitate the expansion of said cells.

The present invention also provides a composition comprising CD34<+> hematopoietic cells in a serum-free, eukaryotic cell culture medium prepared by the present invention.

In accordance with the present invention there may be employed conventional molecular biology, microbiology, and recombinant DNA techniques within the skill of the art. Such techniques are explained fully in the literature. See, e.g., Maniatis, Fritsch and Sambrook, "Molecular Cloning: A Laboratory Manual (1982)) and "Animal Cell Culture" (R. I. Freshney, ed. (1986)).

Those skilled in the art will recognize, or be able to ascertain using no more than routine experimentation, many equivalents to the specific embodiments of the invention described herein. Such equivalents are intended to be encompassed by the following claims.

EXAMPLES

Materials and Methods

1. Human Umbilical Cord Blood Samples

The UCB of full-termed healthy newborns, included uneventful vaginal births or cesarean sections, was harvested with a standard 250-ml blood bag containing citrate-phosphate-dextrose-adenine anticoagulant (Terumo, Shibuya-ku, Tokyo, Japan). The period between collection of UCB samples and their subsequent processing did not exceed 24 h.

2. CD34<+> Cell Enrichment

Buffy coat cells were obtained from UCB samples by centrifugation (700×g for 20 min), and were diluted with an equal volume of wash buffer (Dulbecco's phosphate buffered saline (D-PBS, Sigma, St. Louis, Mo.) contain 2 mM EDTA (Sigma)). Then the Buffy coat cells were layered onto Ficoll-Paque ($\rho$=1.077 g/ml, Amersham Biosciences, Uppsala, Sweden) density gradients to deplete red blood cells (RBC) (700×g for 40 min). The mononuclear cell (MNC) interface was collected, diluted into four volumes of wash buffer, and centrifuged to pellet the cells (700×g for 10 min). The MNC pellet was washed twice and resuspended in MACS buffer (D-PBS contained 0.5% bovine serum albumin (BSA, Sigma) and 2 mM EDTA) for CD133<+> cell purification. CD133<+> cord blood cells were isolated using the Miltenyi VarioMACS device (Miltenyi Biotec, Bergisch Gladbach, Germany), according to the manufacturer's instruction. Briefly, UCB MNC were incubated for 30 min at 4° C. with human IgG to block the Fc receptors and mouse monoclonal antibody to human CD133 microbead (Miltenyi Biotec). Labeled cells were applied to magnetic column (LS column, Miltenyi Biotec). Then, unbound cells were washed out, and CD133<+> cells were eluted from the column with MACS buffer. To improve the purity of the CD133+ (or CD34<+>) cells, a secondary purification cycle was performed with the same way. Then the cells were sampled for CD34<+> analysis to determine yield, purity and viability and assayed for colony-forming cells (CFC) as day 0 for control. To expand cells, CD133<+> cells were seeded at a concentration of 5×10$^4$ cells/ml in 24-well plate (1 ml per well, Falcon, N.J.) with variable serum substitutes, cytokines and medium according to experiment design. After 7 days, the cells were analyzed to compare with the day 0 control (all experiments were repeated at least four times).

3. Growth Factors

The following recombinant human growth factors were tested: thrombopoietin (TPO), stem cell factor (SCF), Flt-3 ligand (FL), interleukin (IL)-3, granulocyte-macrophage colony-stimulating factor (GM-CSF), granulocyte colony-stimulating factor (G-CSF), erythropoietin (EPO) were purchased from Pepro Tech EC Ltd. (NJ, USA). IL-6 and IL-6 sR (soluble receptor) were purchased from R&D systems (Minneapolis, USA).

4. Chemicals

Meat peptone (Difco, Sparks, Md.) was dissolved in water and filtered by 0.2 m membrane before being added into the culture medium. BSA, glutamine, hydrocortisone (HC) and insulin were purchased from Sigma. Albumax I, 2-mercaptoethanol (2-ME) and glutamine were purchased from Gibco BRL (NY, USA). Transferrin (TF) was obtained from Pepro Tech.

5. Medium Preparation

Iscove's modified Dulbecco's medium (IMDM), RPMI 1640 medium, McCoy's 5A medium, Minimum essential medium alpha medium (alpha-MEM), Basal Medium Eagle (BME), Dulbecco's modified Eagle medium (DMEM), Fischer's medium, Medium199 and F-12K nutrient mixture medium (Kaighn's modification, F-12K) were purchased from Gibco BRL. X-vivo 20™ media was purchased from BioWhittaker (Maryland, USA). Stemline™ Hematopoietic stem cell expansion medium (Stemline) was purchased from Sigma. Stemspan™H2000 contained Stemspan™CC100 medium (cytokine cocktail of 100 ng/ml FL, 100 ng/ml SCF, 20 ng/ml IL-3 and 20 ng/ml IL-6) (H2000+CC100) was purchased from StemCell Tech. (Vancouver, Canada).

6. Colony-Forming Unit Assay

Hematopoietic progenitor cells before and after culture were plated in semisolid culture (MethoCult™ GF H4434, StemCell Tech.) following the manufacturer's instruction for colony-forming unit assay. The cells were plated at suitable concentrations (to give <100 colonies per 1 ml culture) in IMDM containing 1% methylcellulose, 30% fetal bovine serum (FBS), 1% BSA, 10-4M 2-ME, 2 mM l-glutamine, 50 ng/ml rhSCF, 10 ng/ml rhIL-3, 10 ng/ml rhGM-CSF, and 3 μml rhEPO. Methylcellulose cultures were aliquotted in 1.1 ml volumes in 35 mm petri dishes (Corning, N.Y., USA) and were then incubated at 37° C. in an atmosphere of 5% CO2 and humidified incubator. After 12-14 days of culture, burst-forming unit-erythroid (BFU-E), colony-forming unitgranulocyte/macrophage (CFU-GM), and colony-forming unit-granulocyte/erythroid/macrophage/megakaryocyte (CFU-GEMM) were scored by an inverted microscope.

7. Flow Cytometry Analysis of CD34<+> Cells

Cells before and after expanding culture were analyzed by two-color flow cytometry on a FACSCaliber analyzer (Becton-Dickinson, NJ, USA). About 1×10$^6$ cells were stained with FITC-conjugated anti-human CD45 and Peconjugated anti-human CD34, and gated for CD45<+>CD34<+> cells with low side scatter, according to the CD34 enumeration protocols developed by the International Society of Hematotherapy and Graft Engineering (ISHAGE) (Sutherland Dr, et al, *J Hematother* 1996; 5:231-8). A replicate sample was stained with FITC-antiCD45 and PE-mouse IgG1 as an isotype control to ensure specificity.

7. Experimental Design and Statistical Analysis

Two-level factorial design followed the method of steepest ascent was carried out to find the optimal concentration of serum substitutes and cytokines for CD34<+> cells expansion. Fractional and full factorial design data were regressed by SPSS software (SPSS Inc. In: SPSS for Windows, base system user's guide. Release 6.0. Chicago, Ill.: SPSS Inc.; 1993. p. 235-47) to obtain the first order polynomial. Its statistical significance was determined by an F-test and the significance of the regression coefficients was analyzed by a t-test. The polynomial takes the form of $$\text{White blood cell or CD34<+> cell (cells/ml)} = \beta_0 + \beta_i X_i \quad (1)$$

where β's are the regression constants and X's are coded variables for the tested additives. The regression model can identify the most effective ingredients and can give the information to construct the steepest ascent path to obtain the optimal medium composition for CD34<+> cells expansion.

In the following examples, the development strategy of serum-free and cytokine-containing media is as follows: (1) find the optimal concentration of cytokine combinations in the IMDM containing 10% FBS; (2) find the optimal concentration of serum substitutes to replace serum in the IMDM medium; (3) find the optimal concentration of cytokine combinations again in the IMDM containing serum substitutes; (4) compare different basal medium and commercial medium.

Example 1

Characteristics of the Cell Isolation

Over 80 cord blood samples were isolated. The average volume (blood and anticoagulant) was 142 ml (range: 111-173 ml), containing on average $1.67 \times 10^9$ WBC (range: $9.72 \times 10^8$ to $2.37 \times 10^9$ WBC/ml). After the buffy coat cells were centrifuged over Ficoll-Paque to deplete erythrocytes, the mean recovery of MNC was 30.42% (range: 20.93-38.89%) and the fraction of CD34<+> cells in MNC was 0.86% (range: 0.42-1.28%). Purified CD34<+> cells were isolated from MNC using a Miltenyi VarioMACS device. Both mouse monoclonal antibody to human CD133 microbead and CD34 microbead were tested, and the purity of the recovered cells was analyzed. The purity of CD34<+> cells separated by CD133 antigen was always higher than those separated by CD34 antigen (data not shown). Therefore, human CD133 microbead was used in subsequent experiments. After the cells were isolated using the MACS device, a mean of $3.87 \times 10^6$ MNC (range: $5.8 \times 10^5$ to $7.16 \times 10^6$) was obtained; the average CD34<+> purity was 91.27% (range: 89.14-97.42%), and the average recovery yield of CD34<+> cells from the initial MNC was 95.31% (range: 90.58-99.99%).

Example 2

Cytokines Screening in Serum-Containing Medium

Nine kinds of cytokines, SCF, FL or IL-3, IL-6, SCF, FL, IL-6 sR, GM-CSF, G-CSF, TPO and EPO were selected for screening.

The $2^{9-5}$ fractional factorial design (16 runs simultaneously) was adopted here to determine what cytokines are required in the hematopoietic expansion culture. In this study, the basal medium was IMDM that contained 10% FBS; the initial cell density was $5 \times 10^4$ cells/ml and the cells were analyzed after one-week culture. Table 4 lists the coded level of each cytokines, WBC growth and CD34<+> cell growth.

TABLE 4

Matrix of the $2^{9-5}$ fractional factorial design and experiment results.

| Trial | TPO | IL-3 | SCF | FL | G-CSF | GM-CSF | IL-6 | IL-6 sR | EPO | WBC C.D$^b$ (10$^6$/ml) | CD34<+> C.D$^b$ (10$^6$/ml) |
|---|---|---|---|---|---|---|---|---|---|---|---|
| 1  | −1 | −1 | −1 | −1 | −1 | −1 | −1 | −1 | +1 | 0.2 | 0.15 |
| 2  | +1 | −1 | −1 | −1 | +1 | −1 | +1 | +1 | −1 | 0.7 | 0.28 |
| 3  | −1 | +1 | −1 | −1 | +1 | +1 | −1 | +1 | −1 | 1.0 | 0.31 |
| 4  | +1 | +1 | −1 | −1 | −1 | +1 | +1 | −1 | +1 | 1.6 | 0.42 |
| 5  | −1 | −1 | +1 | −1 | +1 | +1 | +1 | −1 | −1 | 3.0 | 0.80 |
| 6  | +1 | −1 | +1 | −1 | −1 | +1 | −1 | +1 | +1 | 2.4 | 0.91 |
| 7  | −1 | +1 | +1 | −1 | −1 | −1 | +1 | +1 | +1 | 2.7 | 0.92 |
| 8  | +1 | +1 | +1 | −1 | +1 | −1 | −1 | −1 | −1 | 3.0 | 1.17 |
| 9  | −1 | −1 | −1 | +1 | −1 | −1 | −1 | +1 | −1 | 1.0 | 0.37 |
| 10 | +1 | −1 | −1 | +1 | +1 | −1 | +1 | −1 | +1 | 2.4 | 0.68 |
| 11 | −1 | +1 | −1 | +1 | +1 | +1 | −1 | −1 | +1 | 1.9 | 0.56 |
| 12 | +1 | +1 | −1 | +1 | −1 | +1 | +1 | +1 | −1 | 2.0 | 0.67 |
| 13 | −1 | −1 | +1 | +1 | +1 | +1 | +1 | +1 | +1 | 2.6 | 0.94 |
| 14 | +1 | −1 | +1 | +1 | −1 | +1 | −1 | −1 | −1 | 2.9 | 1.43 |
| 15 | −1 | +1 | +1 | +1 | −1 | −1 | +1 | −1 | −1 | 3.1 | 1.13 |
| 16 | +1 | +1 | +1 | +1 | +1 | −1 | −1 | +1 | +1 | 3.2 | 1.34 |

$^a$−1: no addition; +1: the concentration of adding cytokine is 100 ng/ml except EPO is 2 U/ml; the initial seed density was $5 \times 10^4$ cells/ml.
$^b$C.D: cell density at day 7.

The results of the linear first-order models were obtained according to the data of Table 4.

$$10^6 \text{ WBC cells/ml} = 2.106 + 0.169x1 + 0.206x2 + 0.756x3 + 0.281x4 + 0.119x5 + 0.106x6 + 0.019x7 - 0.156x8 + 0.018x9 \quad (2)$$

$$10^6 \text{ CD34<+> cells/ml} = 0.759 + 0.109x1 + 0.06x2 + 0.326x3 + 0.136x4 + 0.004x5 - 0.009x6 + 0.001x7 - 0.038x8 - 0.014x9 \quad (3)$$

where x1, x2, x3, x4, x5, x6, x7, x8, and x9 are coded variables for TPO, IL-3, SCF, FL, G-CSF, GM-CSF, IL-6, IL-6 sR, and EPO, respectively. Eq. (2) specifies that all cytokines can promote WBC growth except IL-6 sR. TPO, IL-3, SCF, and FL had stronger effects than the other cytokines because of their larger positive coefficients, and IL-6 sR was the only one that inhibited WBC growth owing to its negative coefficient. With respect to the CD34<+> cell growth, Eq. (3) specifies that TPO, IL-3, SCF and FL can stimulate CD34<+> cell expansion. Adding G-CSF and IL-6 to serum-containing IMDM had less positive effects than TPO, IL-3, SCF and FL. In particular, the effects of GM-CSF and EPO on the CD34<+> cell expansion were negative, but were positive on WBC cell growth.

The $2^{9-5}$ fractional factorial design demonstrated that TPO, IL-3, SCF and FL were important and positively affected both WBC and CD34<+> cell growth, and they were then evaluated by the $2^{4-1}$ fractional factorial design. The coded level of each cytokines, WBC growth and CD34<+> cell growth were listed in Table 5, and the result of the linear first-order models were obtained based on the data of Table 5.

TABLE 5

Matrix of the $2^{4-1}$ fractional factorial design and experiment results[a]

| Trial | TPO | IL-3 | SCF | FL | WBC C.D[b] ($10^6$/ml) | CD34<+> C.D[b] ($10^6$/ml) |
|---|---|---|---|---|---|---|
| 1 | −1 | −1 | −1 | −1 | 0.2 | 0.06 |
| 2 | +1 | −1 | −1 | +1 | 1.0 | 0.38 |
| 3 | −1 | +1 | −1 | +1 | 0.8 | 0.23 |
| 4 | +1 | +1 | −1 | −1 | 0.9 | 0.21 |
| 5 | −1 | −1 | +1 | +1 | 0.7 | 0.22 |
| 6 | +1 | −1 | +1 | −1 | 1.3 | 0.49 |
| 7 | −1 | +1 | +1 | −1 | 1.1 | 0.33 |
| 8 | +1 | +1 | +1 | +1 | 2.9 | 1.14 |

[a]−1: no addition; +1: the concentration of adding cytokine is 10 ng/ml; the initial seed density was $5 \times 10^4$ cells/ml.
$10^6$ WBC cells/ml = $1.113 + 0.413x_1 + 0.313x_2 + 0.387x_3 + 0.237x_4$ (4)
$10^6$ CD34<+> cells/ml = $0.388 + 0.172x_1 + 0.100x_2 + 0.162x_3 + 0.110x_4$ (5)

where x1, x2, x3, and x4 are coded variables for TPO, IL-3, SCF, and FL, respectively.

Both Eqs. (4) and (5) show that TPO, IL-3, SCF and FL all facilitated WBC and CD34<+> cell growth, and the most important cytokine was TPO. A steepest ascent path for WBC and CD34<+> cell growth was designed to obtain the optimal concentrations of TPO, IL-3, SCF, and FL to be added to the serum-containing medium. The steepest ascent path was designed according to Eq. (5) and Table 6 shows the results. The starting concentrations of TPO, IL-3, SCF and FL in steepest ascent method were set as the half value of the concentrations in 2-level (fractional) factorial design (Trail 1 in Table 6). Along the path of steepest ascent method, the TPO, IL-3, SCF and FL operating concentrations were increased in a ratio of "1.72:1:1.62:1.1" each trail, and were slightly modified to make the values more easily being calculated.

TABLE 6

The concentrations of TPO, IL-3, SCF and FL along the steepest ascent path for WBC and CD34<+> cell growth in the serum-containing medium[a]

| Trial | TPO (ng/ml) | IL-3 (ng/ml) | SCF (ng/ml) | FL (ng/ml) | WBC C.D[b] (106/ml) | CD34<+> C.D[b] (106/ml) |
|---|---|---|---|---|---|---|
| 1 | 5.0 | 5.0 | 5.0 | 5.0 | 1.2 (0.01) | 0.62 (0.03) |
| 2 | 14.0 | 10.0 | 13.5 | 10.8 | 2.3 (0.20) | 1.12 (0.12) |
| 3 | 23.1 | 15.0 | 22.0 | 16.5 | 2.4 (0.25) | 1.13 (0.11) |
| 4 | 32.1 | 20.0 | 30.5 | 22.3 | 2.9 (0.20) | 1.25 (0.08) |
| 5 | 41.2 | 25.0 | 39.0 | 28.0 | 2.9 (0.30) | 1.20 (0.08) |
| 6 | 50.2 | 30.0 | 47.5 | 33.8 | 2.9 (0.15) | 1.26 (0.04) |
| 7 | 59.3 | 35.0 | 56.0 | 39.5 | 3.1 (0.25) | 1.33 (0.04) |
| 8 | 68.3 | 40.0 | 64.5 | 45.3 | 3.0 (0.25) | 1.28 (0.02) |

[a]Value in the parenthesis was the standard deviation; the initial seed density was $5 \times 10^4$ cells/ml.
[b]C.D: cell density at day 7.

After the step 4 medium, result indicates that further increasing the concentration of the cytokines could not significantly increase the WBC and CD34<+> cell growth. Consequently, the optimal concentration of the cytokine combination in the IMDM that contained 10% FBS were supplemented with TISF cocktail (32.1 ng/ml TPO, 20 ng/ml IL-3, 30.5 ng/ml SCF, and 22.3 ng/ml FL (cytokine cocktail of step 4)).

Example 3

Serum Substitutes Screening Based on Cytokines-Containing Medium

Eight kinds of compounds that are very often used as serum substitutes were selected: BSA, Albumax I, TF, insulin, HC, 2-ME, glutamine and peptone.

The $2^{8-4}$ fractional factorial design was used to identify the serum substitutes required in the hematopoietic expansion culture. In this study, the basal medium was IMDM medium containing TISF as developed above; the initial cell density was $5 \times 10^4$ cells/ml and the cells were analyzed after one-week culture. Table 7 describes the design, and two first-order models were obtained.

TABLE 7

Matrix of the $2^{8-4}$ fractional factorial design and experiment results[a]

| Trial | Albumax (10 g/l) | BSA (10 g/l) | TF (0.4 g/l)F | Glutamine (2 mN) | HC (1 mg/l) | Peptone (1 g/l) | 2-ME (55 μM) | Insulin | WBC C.D[b] ($10^6$/ml) | CD34<+> C.D[b] ($10^5$/ml) |
|---|---|---|---|---|---|---|---|---|---|---|
| 1 | −1 | −1 | −1 | −1 | −1 | −1 | −1 | −1 | 0.3 | 2.47 |
| 2 | +1 | −1 | −1 | −1 | +1 | −1 | +1 | +1 | 0.9 | 3.07 |

TABLE 7-continued

Matrix of the $2^{8-4}$ fractional factorial design and experiment results[a]

| Trial | Albumax (10 g/l) | BSA (10 g/l) | TF (0.4 g/l)F | Glutamine (2 mN) | HC (1 mg/l) | Peptone (1 g/l) | 2-ME (55 μM) | Insulin | WBC C.D[b] ($10^6$/ml) | CD34<+> C.D[b] ($10^5$/ml) |
|---|---|---|---|---|---|---|---|---|---|---|
| 3 | −1 | +1 | −1 | −1 | +1 | +1 | −1 | +1 | 1.6 | 5.89 |
| 4 | +1 | +1 | −1 | −1 | −1 | +1 | +1 | −1 | 0.9 | 2.96 |
| 5 | −1 | −1 | +1 | −1 | +1 | +1 | +1 | −1 | 0.7 | 2.17 |
| 6 | +1 | −1 | +1 | −1 | −1 | +1 | −1 | +1 | 0.3 | 1.54 |
| 7 | −1 | +1 | +1 | −1 | −1 | −1 | +1 | +1 | 1.1 | 4.79 |
| 8 | +1 | +1 | +1 | −1 | +1 | −1 | −1 | −1 | 1.1 | 4.74 |
| 9 | −1 | −1 | −1 | +1 | −1 | −1 | −1 | +1 | 0.3 | 1.35 |
| 10 | +1 | −1 | −1 | +1 | +1 | −1 | +1 | −1 | 0.3 | 1.29 |
| 11 | −1 | +1 | −1 | +1 | +1 | +1 | −1 | −1 | 0.8 | 3.21 |
| 12 | +1 | +1 | −1 | +1 | −1 | +1 | +1 | +1 | 0.9 | 3.09 |
| 13 | −1 | −1 | +1 | +1 | +1 | +1 | +1 | +1 | 0.8 | 3.14 |
| 14 | +1 | −1 | +1 | +1 | −1 | +1 | −1 | −1 | 0.5 | 1.70 |
| 15 | −1 | +1 | +1 | +1 | −1 | −1 | +1 | −1 | 1.2 | 3.90 |
| 16 | +1 | +1 | +1 | +1 | +1 | −1 | −1 | +1 | 1.3 | 3.27 |

[a]−1: no addition; +1: adding the indicated amount of additives; the initial seed density was $5 \times 10^4$ cells/ml.
[b]C.D: cell density at day 7.
$10^5$ WBC cells/ml = $8.5 + 2.625x2 + x3 - 0.875x4 + 0.5x5 - 0.375x6 + 0.875x7 + 1.250x8$ (6)
$10^5$ CD34<+> cells/ml = $3.036 - 0.329x1 + 0.945x2 + 0.120x3 - 0.418x4 - 0.240x5 - 0.221x6 + 0.311x7 + 0.231x8$ (7)

where x1, x2, x3, x4, x5, x6, x7, and x8 are coded variables for Albumax I, BSA, TF, glutamine, HC, peptone, 2-ME, and insulin, respectively. According to Eqs. (6) and (7), the four most significant serum substitutes that can stimulate both WBC and CD34<+> cell growth were BSA, TF, 2-ME, and insulin. The others were inhibitors of WCB or/and CD34<+> cell growth. Then BSA, TF, 2-ME and insulin were evaluated using the $2^4$ full factorial design (Table 8), and the results of the linear first-order models were obtained based on the data of Table 8.

TABLE 8

Matrix of the $2^4$ full factorial design and experiment results[a]

| Trial | BSA (10 g/l) | Insulin (10 μg/ml) | TF (0.4 g/l) | 2-ME (55 μM) | WBC C.D[b] ($10^6$/ml) | CD34<+> C.D[b] ($10^5$/ml) |
|---|---|---|---|---|---|---|
| 1 | −1 | −1 | −1 | −1 | 0.4 | 0.28 |
| 2 | −1 | −1 | +1 | −1 | 2.3 | 1.19 |
| 3 | −1 | −1 | −1 | +1 | 0.4 | 0.29 |
| 4 | −1 | −1 | +1 | +1 | 2.5 | 1.24 |
| 5 | −1 | +1 | −1 | −1 | 0.4 | 0.25 |
| 6 | −1 | +1 | +1 | −1 | 2.4 | 1.14 |
| 7 | −1 | +1 | −1 | +1 | 0.4 | 0.29 |
| 8 | −1 | +1 | +1 | +1 | 2.5 | 1.21 |
| 9 | +1 | −1 | −1 | −1 | 1.3 | 0.92 |
| 10 | +1 | −1 | +1 | −1 | 2.2 | 1.37 |
| 11 | +1 | −1 | −1 | +1 | 1.5 | 1.03 |
| 12 | +1 | −1 | +1 | +1 | 2.6 | 1.57 |
| 13 | +1 | +1 | −1 | −1 | 2.1 | 1.43 |
| 14 | +1 | +1 | +1 | −1 | 2.5 | 1.51 |
| 15 | +1 | +1 | −1 | +1 | 2.2. | 1.39 |
| 16 | +1 | +1 | +1 | +1 | 2.7 | 1.50 |

[a]−1: no addition; +1: adding the indicated amount of additives; the initial seed density was $5 \times 10^4$ cells/ml.
[b]C.D: cell density at day 7.
$10^6$ WBC cells/ml = $1.8 + 0.362x1 + 0.131x2 + 0.7x3 + 0.069x4$ (8)
$10^6$ CD34<+> cells/ml = $1.043 + 0.302x1 + 0.053x2 + 0.303x3 + 0.025x4$ (9)

where x1, x2, x3, and x4 are coded variables for BSA, insulin, TF and 2-ME, respectively. Both Eqs. (8) and (9) specify that BSA, insulin, TF, and 2-ME were necessary components in serum-free medium and could promote WBC and CD34<+> cell growth instead of serum. BSA and TF dominated the CD34<+> cell expansion. The optimal concentrations of these four kinds of serum substitutes were made along the steepest ascent path according to Eq. (9) and the results were listed on Table 9. The starting concentrations of BSA, insulin, TF and 2-ME in steepest ascent method were set as the half value of the concentrations in 2-level (fractional) factorial design (Trail 13 in Table 9). Along the path of steepest ascent method, the BSA, insulin, TF and 2-ME operating concentrations were increased or decreased in a ratio of "5.7:1:228.7:2.6" each trail, and were slightly modified to make the values more easily being calculated. WBC and CD34<+> cell densities increased when the concentrations increased along the step initially, and then reached a plateau in step 6. Finally, WBC and CD34<+> cell densities declined after step 11. Consequently, the optimal concentration of the serum substitute combination in the TISF medium was supplemented with BIT2 (serum substitute cocktail in step 6: 1.5 g/l BSA, 4.39 g/ml insulin, 60 g/ml transferrin, and 25.94 μM 2-ME).

TABLE 9

The concentrations of BSA, insulin, TF and 2-ME along the steepest ascent path for WBC and CD34<+> cell growth in the cytokines-containing medium[a]

| Trial | BSA (g/l) | Insulin (μg/ml) | TF (μg/ml) | 2-ME (μM) | WBC C.D[b] (10$^6$/ml) | CD34<+> C.D[b] (10$^5$/ml) |
|---|---|---|---|---|---|---|
| 1 | 0.2 | 4.16 | 8 | 25.37 | 1.9 (0.18) | 4.68 (0.53) |
| 2 | 0.4 | 4.20 | 16 | 25.45 | 2.1 (0.15) | 5.10 (0.55) |
| 3 | 0.6 | 4.23 | 24 | 25.54 | 2.3 (0.13) | 5.90 (0.60) |
| 4 | 0.8 | 4.27 | 32 | 25.63 | 2.3 (0.13) | 6.00 (0.56) |
| 5 | 1.0 | 4.30 | 40 | 25.72 | 2.3 (0.14) | 5.88 (0.55) |
| 6 | 1.5 | 4.39 | 60 | 25.94 | 2.3 (0.14) | 7.06 (0.71) |
| 7 | 2.0 | 4.48 | 80 | 26.17 | 2.4 (0.13) | 6.84 (0.66) |
| 8 | 2.5 | 4.56 | 100 | 26.39 | 2.4 (0.13) | 6.55 (0.34) |
| 9 | 3.0 | 4.65 | 120 | 26.61 | 2.4 (0.13) | 6.55 (0.39) |
| 10 | 3.5 | 4.74 | 140 | 26.83 | 2.4 (0.16) | 6.49 (0.52) |
| 11 | 4.0 | 4.83 | 160 | 27.06 | 2.4 (0.15) | 7.33 (0.41) |
| 12 | 4.5 | 4.91 | 180 | 27.28 | 2.4 (0.15) | 6.86 (0.66) |
| 13 | 5.0 | 5.00 | 200 | 27.50 | 2.3 (0.14) | 6.66 (0.52) |
| 14 | 7.5 | 5.44 | 300 | 28.61 | 2.0 (0.14) | 6.57 (0.79) |
| 15 | 10.0 | 5.87 | 400 | 29.72 | 1.8 (0.11) | 6.06 (0.55) |
| 16 | 12.5 | 6.31 | 500 | 30.84 | 1.7 (0.13) | 5.84 (0.70) |

[a]Value in the parenthesis was the standard deviation; the initial seed density was $5 \times 10^4$ cells/ml.
[b]C.D: cell density at day 7.

Example 4

Optimal Quantity of Cytokines in the Serum-Free Medium (IMDM+BIT2)

In this study, nine kinds of cytokines were tested in the serum-free medium that was developed. The $2^{9-5}$ fractional factorial design was used again to determine which cytokine could stimulate WBC and CD34<+> cell growth. The $2^{9-5}$ fractional factorial design was the same as the design for serum-containing serum (Table 4) except in that the basal medium was changed to IMDM that contained BIT2. Seven cytokines including TPO, IL-3, SCF, FL, IL-6, G-CSF, and GM-CSF could facilitate WBC and CD34<+> cell growth (data not shown). These seven cytokines were then analyzed using the $2^{7-3}$ fractional factorial design to determine the steepest ascent path (Table 10).

The results of the linear first-order models were obtained based on the data of Table 10.

$$10^6 \text{ WBC cells/ml}=0.807+0.292x1+0.149x2+ \\ 0.431x3+0.164x4+0.016x5+0.128x6+0.078x7 \qquad (10)$$

$$10^5 \text{ CD34<+> cells/ml}=2.945+0.857x1+0.415x2+ \\ 1.523x3+0.685x4+0.078x5+0.320x6+0.132x7 \qquad (11)$$

where x1, x2, x3, x4, x5, x6, and x7 are coded variables for TPO, IL-3, SCF, FL, IL-6, G-CSF and GM-CSF, respectively. These seven cytokines all positively affected WBC and CD34<+> cell growth in the order, SCF>TPO>FL>IL-3>G-CSF>GM-CSF>IL-6. The optimal concentrations of seven cytokines in the serum-free medium were determined along the steepest ascent path according to Eq. (11) and the results were listed in Table 11. Because the WBC or CD34<+> cells were proved that could bare the culture condition with low concentration or without growth factors. The starting concentrations of TPO, IL-3, SCF, FL, IL-6, G-CSF and GM-CSF in steepest ascent method were set as zero, and then increased in a ratio of "11:5.3:19.5:8.8:1:4.1:1.7" each trail (Trail 1 in Table 11). The concentrations were slightly modified to make the values more easily being calculated. WBC and CD34<+> cell growth initially increased with cytokine concentration, reaching $3.18 \times 10^6$ and $1.34 \times 10^6$ cells/ml in step 6 (cytokine cocktail of step 6 (CC-S6): 8.46 ng/ml TPO, 4.09 ng/ml IL-3, 15 ng/ml SCF, 6.73 ng/ml FL, 0.78 ng/ml IL-6, 3.17 ng/ml G-CSF, and 1.30 ng/ml GM-CSF, respectively). After step 6, no more increases in WBC or CD34<+> cell density was observed.

TABLE 10

Matrix of the $2^{7-3}$ fractional factorial design and experiment results[a]

| Trial | TPO | IL-3 | SCF | FL | IL-6 | G-CSF | GM-CSF | WBC C.D[b] (10$^6$/ml) | CD34<+> C.D[b] (10$^5$/ml) |
|---|---|---|---|---|---|---|---|---|---|
| 1 | −1 | −1 | −1 | −1 | −1 | −1 | −1 | 0.1 | 0.43 |
| 2 | +1 | −1 | −1 | −1 | +1 | −1 | +1 | 0.3 | 1.05 |
| 3 | −1 | +1 | −1 | −1 | +1 | +1 | −1 | 0.2 | 0.85 |
| 4 | +1 | +1 | −1 | −1 | −1 | +1 | +1 | 0.6 | 1.33 |
| 5 | −1 | −1 | +1 | −1 | +1 | +1 | +1 | 0.8 | 2.28 |
| 6 | +1 | −1 | +1 | −1 | −1 | +1 | −1 | 1.1 | 4.53 |
| 7 | −1 | +1 | +1 | −1 | −1 | −1 | +1 | 0.6 | 2.71 |
| 8 | +1 | +1 | +1 | −1 | +1 | −1 | −1 | 1.5 | 4.90 |
| 9 | −1 | −1 | −1 | +1 | −1 | +1 | +1 | 0.4 | 1.31 |
| 10 | +1 | −1 | −1 | +1 | +1 | +1 | −1 | 0.6 | 2.57 |
| 11 | −1 | +1 | −1 | +1 | +1 | −1 | +1 | 0.3 | 1.87 |
| 12 | +1 | +1 | −1 | +1 | −1 | −1 | −1 | 0.6 | 1.97 |
| 13 | −1 | −1 | +1 | +1 | +1 | −1 | −1 | 0.4 | 2.33 |
| 14 | +1 | −1 | +1 | +1 | −1 | −1 | +1 | 1.6 | 5.74 |
| 15 | −1 | +1 | +1 | +1 | −1 | +1 | −1 | 1.4 | 4.92 |
| 16 | +1 | +1 | +1 | +1 | +1 | +1 | +1 | 2.5 | 8.33 |

[a]−1: no addition; +1: the concentration of added cytokine is 100 ng/ml; the initial seed density was $5 \times 10^4$ cells/ml.
[b]C.D: cell density at day 7.

TABLE 11

The concentrations of TPO, IL-3, SCF, FL, IL-6, G-CSF, GM-CSF along the steepest ascent path for WBC and CD34+ cell growth in the serum-free medium[a].

| Trial | TPO (ng/ml) | IL-3 (ng/ml) | SCF (ng/ml) | FL (ng/ml) | IL-6 (ng/ml) | G-CSF (ng/ml) | GM-CSF (ng/ml) | WBC C.D[b] ($10^6$/ml) | CD34<+> C.D[b] ($10^6$/ml) |
|---|---|---|---|---|---|---|---|---|---|
| 1 | 1.41 | 0.68 | 2.50 | 1.12 | 0.13 | 0.53 | 0.22 | 1.3 (0.07) | 0.44 (0.11) |
| 2 | 2.82 | 1.36 | 5.00 | 2.24 | 0.26 | 1.06 | 0.43 | 1.8 (0.14) | 0.58 (0.12) |
| 3 | 4.23 | 2.05 | 7.50 | 3.36 | 0.39 | 1.58 | 0.65 | 2.2 (0.28) | 0.84 (0.12) |
| 4 | 5.64 | 2.73 | 10.00 | 4.49 | 0.52 | 2.11 | 0.86 | 2.6 (0.21) | 0.98 (0.11) |
| 5 | 7.05 | 3.41 | 12.50 | 5.91 | 0.65 | 2.64 | 1.08 | 2.7 (0.22) | 1.03 (0.10) |
| 6 | 8.46 | 4.09 | 15.00 | 6.73 | 0.78 | 3.17 | 1.30 | 3.2 (0.16) | 1.34 (0.14) |
| 7 | 9.87 | 4.78 | 17.50 | 7.85 | 0.91 | 3.70 | 1.51 | 2.9 (0.15) | 1.12 (0.10) |
| 8 | 11.28 | 5.46 | 20.00 | 8.97 | 1.04 | 4.22 | 1.73 | 2.8 (0.11) | 1.09 (0.11) |
| 9 | 14.10 | 6.82 | 25.00 | 11.21 | 1.30 | 5.28 | 2.16 | 2.8 (0.13) | 1.08 (0.13) |
| 10 | 16.91 | 8.19 | 30.00 | 13.46 | 1.56 | 6.34 | 2.59 | 2.6 (0.13) | 0.94 (0.13) |
| 11 | 19.73 | 9.55 | 35.00 | 15.70 | 1.82 | 7.39 | 3.02 | 2.9 (0.12) | 1.05 (0.14) |
| 12 | 22.55 | 10.92 | 40.00 | 17.94 | 2.08 | 8.45 | 3.46 | 2.7 (0.13) | 0.94 (0.11) |
| 13 | 25.37 | 12.28 | 45.00 | 20.19 | 2.65 | 9.51 | 3.89 | 2.6 (0.13) | 0.98 (0.12) |
| 14 | 28.19 | 13.65 | 50.00 | 22.43 | 2.61 | 10.56 | 4.32 | 2.7 (0.15) | 0.75 (0.11) |
| 15 | 31.01 | 15.01 | 55.00 | 24.67 | 2.87 | 11.62 | 4.75 | 2.5 (0.14) | 0.65 (0.13) |
| 16 | 33.83 | 16.38 | 60.00 | 26.91 | 3.13 | 12.67 | 5.18 | 2.4 (0.18) | 0.64 (0.16) |

[a]Value in the parenthesis was the standard deviation; the initial seed density was $5 \times 10^4$ cells/ml.
[b]C.D: cell density at day 7.

Figure 2:
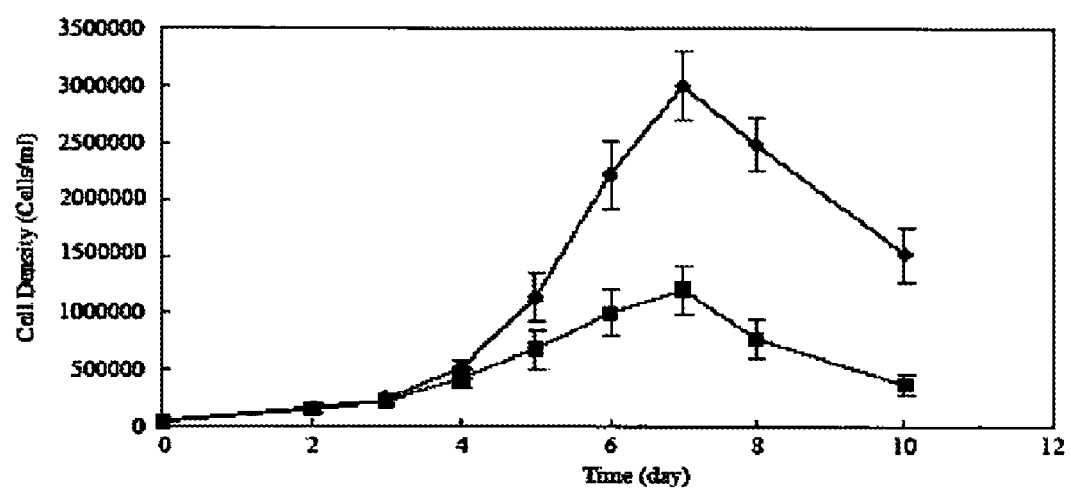
FIG. 2 discloses the growth curve of WBC and CD34<+> cell in the OSFCM and the initial cell density was $5 \times 10^4$ cells/ml. Symbols: (♦), WBC; (■), CD34<+> cell (n=10).

Finally, optimal serum-free and cytokines-containing medium (OSFCM) for the ex vivo expansion of human umbilical cord blood CD34<+> hematopoietic progenitor cells was developed, which is IMDM containing BIT2 and CC-S6. FIG. 2 presents growth profiles of WBC and CD34<+> cells in OSFCM. After one-week culture, the expansions for WBC, CD34<+> cells and CFC were 64-, 27- and 22-fold (Table 12), respectively. The cell viability dropped abruptly after one-week culture. Roβmanith et al used a stroma-free culture combined with the X-vivo 10™ medium and cytokines (TPO, IL-3, SCF and FL) to expand HPC from UCB (Roβmanith et al, Stem Cells 2001; 19:313-20). The amplification of CD34<+> cells and CFC was increased 20.9- and 18.1-fold, respectively. Recently, Denning-Kendall et al used X-vivo 10™ medium and cytokines (TPO, SCF, FL and G-CSF) to expand UCB CD34<+> cells, and the number of total nucleated cells, CD34<+> cells and CFCs increased by an average of 52-, 13- and 7-fold, respectively (Denning-Kendall et al, Stem Cells 2003; 21:61-70). The data presented here are superior to these published results.

While the invention has been described and exemplified in sufficient detail for those skilled in this art to make and use it, various alternatives, modifications, and improvements should be apparent without departing from the spirit and scope of the invention.

One skilled in the art readily appreciates that the present invention is well adapted to carry out the objects and obtain the ends and advantages mentioned, as well as those inherent therein. The embryos, animals, and processes and methods for producing them are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

The invention illustratively described herein suitably may be practiced in the absence of any element or elements, limitation or limitations, which are not specifically disclosed

TABLE 12

The effects of different basal and commercial media on WBC, CD34<+> cell, and CFC expansion[a]

| Basal Medium | Number of Experiments | Cell Growth ($10^6$/ml) | | | CFC ratio B/GM/GEMM[b] | Total CFC expansion fold |
|---|---|---|---|---|---|---|
| | | WBC C.D.[c] | CD34+ C.D[c] | CD34<+> cell | | |
| IMDM | 10 | 3.4 (0.29) | 1.45 (0.19) | 29.0 (3.8) | 32:59:9 | 21.9 (3.07) |
| RPMI 1640 | 6 | 3.3 (0.35) | 1.51 (0.14) | 30.2 (2.8) | 31:60:9 | 17.8 (1.98) |
| McCoy's 5A | 6 | 3.4 (0.32) | 1.61 (0.22) | 32.2 (4.4) | 34:61:5 | 19.7 (6.56) |
| α-MEM | 6 | 2.2 (0.24) | 0.88 (0.05) | 17.6 (1.1) | 12:86:2 | 4.0 (0.39) |
| DMEM | 6 | 1.5 (0.19) | 0.68 (0.03) | 13.6 (0.6) | 32:57:11 | 6.7 (0.42) |
| BME | 6 | 0.8 (0.05) | 0.18 (0.07) | 3.6 (1.4) | 34:49:17 | 1.4 (0.32) |
| Fischer's medium | 6 | 2.4 (0.11) | 0.94 (0.02) | 181.8 (0.4) | 41:56:3 | 16.1 (2.13) |
| Medium 199 | 6 | 0.9 (0.04) | 0.51 (0.01) | 10.2 (0.2) | 32:63:5 | 3.9 (0.73) |
| F-12K | 6 | 3.2 (0.23) | 1.65 (0.13) | 33.0 (2.6) | 34:57:9 | 24.8 (657) |
| Commercial medium | | | | | | |
| X-vivo 20 | 8 | 3.2 (0.41) | 1.53 (0.37) | 30.6 (7.4) | 43:51:6 | 20.3 (1.52) |
| Stemline | 4 | 2.9 (0.11) | 1.40 (0.02) | 28.0 (0.4) | 41:53:6 | 15.4 (2.30) |
| H2000 + CC100 | 10 | 3.4 (0.35) | 1.77 (0.29) | 35.4 (5.8) | 41:54:5 | 17.1 (2.91) |

What is claimed is:

1. A method for producing a serum-free and cytokine-containing cell culture medium for CD34+ hematopoietic cell expansion, said method comprising:
   a) providing CD34+ hematopoietic cells in a first cell culture medium, wherein the first medium is a basal medium supplemented with serum;
   b) finding a optimal kind and concentration of a first cytokine combination for optimal hematopoietic cell growth in the first cell culture medium by using a 2-level factorial design, wherein the 2-level factorial design is an experimental design used to study cell growth in the first cell culture medium supplemented with cytokine(s) and each cytokine at two-levels, present or absent, wherein the cytokine(s) in the cytokine combination has a positive regression coefficient, $\beta$, which is obtained using the 2-level factorial design, and wherein the cytokine combination is selected from the group consisting of IL-3, IL-6, EPO, Flt-3 ligand (FL), SCF, G-CSF, GM-CSF, TPO, and IL-6-sR;
   c) finding a serum substitute combination for optimal hematopoietic cell growth first cell culture medium by using a 2-level factorial design, wherein the 2-level factorial design is an experimental design used to study cell growth in the first cell culture medium supplemented with serum substitute(s) and each serum substitute at two-levels, present or absent, wherein the serum substitute(s) in the serum substitute combination has a positive regression coefficient, $\beta$, which is obtained using the 2-level factorial design, and wherein the serum substitute combination is selected from the group consisting of Lipid-rich bovine serum albumin, BSA (bovine serum albumin), TF (transferrin), glutamine, HC (hydrocortisone), peptone, 2-ME (2-mercaptoethanol) and insulin;
   d) using a steepest ascent method with step changes in the concentration of the cytokine constituent or serum substitute constituent based on foregoing results of 2-level factorial design and evaluating the effects on cell growth, wherein the steepest ascent method is a statistical and mathematical method used to approach the vicinity of the optimal concentration for cell growth;
   e) adopting the changed concentration that gives the most favorable result for CD34+ hematopoietic cell growth; and
   f) producing a second cell culture medium by mixing or admixing a basal medium with the cytokine combination and serum substitute combination at a concentration adopted in step (e), wherein the second cell culture medium is a cytokine-containing and serum-free cell culture medium.

2. The method according to claim 1, wherein the 2-level factorial design or the steepest ascent method is performed using a software package.

3. The method according to claim 2, wherein the software package is SPSS.

4. The method according to claim 1, wherein the basal medium is selected from the group consisting of α-MEM, DMEM, RPMI 1640, IMDM, BME, McCoy's 5A, Fischer's medium, Medium 199 and F-12K.

5. The method according to claim 4, wherein the basal medium is IMDM.

6. The method according to claim 1, wherein the CD34+ cells are obtained from umbilical cord blood, bone marrow, peripheral blood or fetal liver.

7. The method according to claim 6, wherein the CD34+ cells are obtained from umbilical cord blood.

8. The method according to claim 1, wherein CD34+ hematopoietic cells are obtained from a mammal.

9. The method according to claim 8, wherein the CD34+ hematopoietic cells are obtained from human.

* * * * *